United States Patent [19]

Lacefield

[11] 4,013,654
[45] Mar. 22, 1977

[54] 5,6-DIARYL-1,2,4-TRIAZINES

[75] Inventor: William B. Lacefield, Indianapolis, Ind.

[73] Assignee: Eli Lilly and Company, Indianapolis, Ind.

[22] Filed: Mar. 10, 1976

[21] Appl. No.: 665,592

Related U.S. Application Data

[63] Continuation-in-part of Ser. No. 438,156, Jan. 31, 1974, Pat. No. 3,948,894.

[52] U.S. Cl. .......................... 260/248 AS; 424/249
[51] Int. Cl.$^2$ ..................................... C07D 253/06
[58] Field of Search ............................. 260/248 AS

[56] References Cited

OTHER PUBLICATIONS

Neunhoeffer et al., *Ann. der Chemie*, pp. 88–101, vol. 760 (1972).
Neunhoeffer et al., *Chem. Ber.*, pp. 3952–3956, vol. 101 (1968).
Polonovski et al., *Chemical Abstracts*, vol. 46, 514(b) 1952.
Polonovski et al., *Chemical Abstracts*, vol. 47, 11209e (1953).
Laakso et al., *Chem. Abstr.*, vol. 51, 13875i (1957).
Metze et al., *Chem. Abstr.*, vol. 51, 15532d (1957).
Neunhoeffer et al., *Chem. Abstr.*, vol. 75, 129773g (1971).

*Primary Examiner*—John M. Ford
*Attorney, Agent, or Firm*—William E. Maycock; Everet F. Smith

[57] ABSTRACT

5,6-Diaryl-1,2,4-triazines, topically-active anti-inflammatory agents, having the formula,

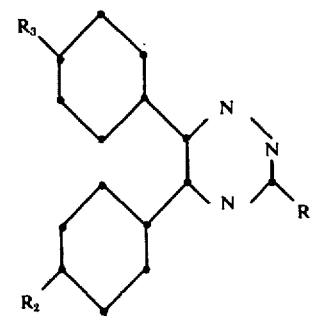

wherein R is hydrogen or —$(X)_nR_1$, in which X is either O or S, n is an integer which is either 0 or 1, and $R_1$ is $C_1$–$C_8$ alkyl, $C_7$–$C_8$ aralkyl, $C_3$–$C_8$ cycloalkyl, or $C_4$–$C_8$ (cycloalkyl)alkyl; and $R_2$ and $R_3$ independently are halo, $C_1$–$C_3$ alkyl, $C_1$–$C_3$ alkoxy, or di($C_1$–$C_3$ alkyl)amino, with the proviso that at least one of $R_2$ and $R_3$ is halo or $C_1$–$C_3$ alkyl; and the pharmaceutically-acceptable acid addition salts of basic members thereof.

13 Claims, No Drawings

5,6-DIARYL-1,2,4-TRIAZINES

CROSS-REFERENCE TO RELATED APPLICATION

This application is a continuation-in-part of copending application Ser. No. 438,156, filed Jan. 31, 1974, now U.S. Pat. No. 3,948,894.

BACKGROUND OF THE INVENTION

This invention relates to anti-inflammatory 5,6-diaryl-1,2,4-triazines. More particularly, this invention relates to topically-active anti-inflammatory 5,6-diaryl-1,2,4-triazines.

Inflammation is an essentially protective and normal response to injury, although the etiology and pathogenesis of many inflammatory conditions remain obscure. In general, anti-inflammatory agents are employed primarily to relieve the symptoms of inflammation. In such symptomatic therapy, topically-applied anti-inflammatory agents present special problems. Inflammatory conditions calling for the topical application of an anti-inflammatory agent are almost exclusively treated with steroids. Topically-applied steroids, however, may carry considerable systemic toxicity. Thus, the need continues for safer, better tolerated topically-active anti-inflammatory agents.

SUMMARY OF THE INVENTION

In accordance with the present invention, 5,6-diaryl-1,2,4-triazines are provided having the formula,

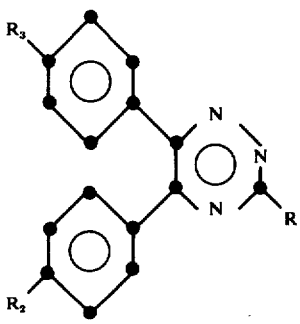

wherein R is hydrogen or $-(X)_nR_1$, in which X is either O or S, n is an integer which is either 0 or 1, and $R_1$ is $C_1-C_8$ alkyl, $C_7-C_8$ aralkyl, $C_3-C_8$ cycloalkyl, or $C_4-C_8$ (cycloalkyl)alkyl; and $R_2$ and $R_3$ independently are halo, $C_1-C_3$ alkyl, $C_1-C_3$ alkoxy or di($C_1-C_3$ alkyl)amino, with the proviso that at least one of $R_2$ and $R_3$ is halo or $C_1-C_3$ alkyl; and the pharmaceutically-acceptable acid addition salts of basic members thereof.

The compounds of the present invention are useful as anti-inflammatory agents. In particular, all of such compounds are especially useful as topically-active anti-inflammatory agents in warm-blooded mammals, such as guinea pigs, mice, rats, dogs, monkeys, humans, and the like. In addition, various compounds wherein X is O or S and n is 1 are useful as intermediates in the preparation of anti-inflammatory 3-amino-5,6-diaryl-1,2,4-triazines which are disclosed and claimed in co-pending and commonly-assigned application Ser. No. 438,156, filed Jan. 31, 1974, by William B. Lacefield, now U.S. Pat. No. 3,948,894.

DETAILED DESCRIPTION OF THE INVENTION

The term $C_1-C_8$ alkyl includes methyl, ethyl, propyl, isopropyl, butyl, isobutyl, sec-butyl, tert-butyl, pentyl, isopentyl, 1-methylbutyl, 1-ethylpropyl, neopentyl, tert-pentyl, 1,2-dimethylpropyl, hexyl, isohexyl, 2-ethylbutyl, 1-ethyl-1;L -methylpropyl, heptyl, 2-ethyl-1-methylbutyl, 2,4-dimethylpentyl, octyl, 2-ethylhexyl, 1,1-diethylbutyl, and the like.

The term $C_7-C_8$ aralkyl includes benzyl, 2-phenylethyl, p-methylbenzyl, m-methylbenzyl, o-methylbenzyl, and the like.

The term $C_3-C_8$ cycloalkyl includes cyclopropyl, 2-butylcyclopropyl, cyclobutyl, 2-ethyl-3-methylcyclobutyl, cyclopentyl, 3-isopropylcyclopentyl, cyclohexyl, 1-methylcyclohexyl, 2,5-dimethylcyclohexyl, cycloheptyl, 5-methylcycloheptyl, cyclooctyl, and the like.

The term $C_4-C_8$ (cycloalkyl)alkyl includes cyclopropylmethyl, 3-cyclopropyl-2-methylbutyl, 3-(2-methylcyclobutyl)propyl, 2-cyclopentylethyl, 4-methylcyclohexylmethyl, cycloheptylmethyl, and the like.

The term $C_1-C_3$ alkoxy includes methoxy, ethoxy, propoxy, and isopropoxy. The term $C_1-C_3$ alkyl includes methyl, ethyl, propyl, and isopropyl. The term halo includes fluoro, chloro, bromo, and iodo.

Illustrative of the triazine compounds which are provided by the present invention are the following:
5,6-bis(4-fluorophenyl)-1,2,4-triazine,
5,6-bis(4-fluorophenyl)-3-methyl-1,2,4-triazine,
5,6-bis(4-fluorophenyl)-3-methoxy-1,2,4-triazine,
5,6-bis(4-fluorophenyl)-3-methylthio-1,2,4-triazine,
5,6-bis(4-methylphenyl)-1,2,4-triazine,
3-methyl-5,6-bis(4-methylphenyl)-1,2,4-triazine,
3-methoxy-5,6-bis(4-methylphenyl)-1,2,4-triazine,
5,6 -bis(4-methylphenyl)-3-methylthio-1,2,4-triazine,
6-(4-bromophenyl)-5-(4-iodophenyl)-1,2,4-triazine,
5-(4-ethylphenyl)-6-(4-propylphenyl)-1,2,4-triazine,
6-(4-fluorophenyl)-5-(4-methylphenyl)-1,2,4-triazine,
5-(4-methoxyphenyl)-6-(4-methylphenyl)-1,2,4-triazine,
5-(4-diethylaminophenyl)-6-(4-fluorophenyl)-1,2,4-triazine,
5-(4-fluorophenyl)-3-methyl-6-(4-methylphenyl)-1,2,4-triazine,
6-(4-fluorophenyl)-3-methoxy-5-(4-methylphenyl)-1,2,4-triazine,
5-(4-methoxyphenyl)-6-(4-methylphenyl)-3-methylthio-1,2,4-triazine,
6-(4-dimethylaminophenyl)-3-methyl-5-(4-methylphenyl)-1,2,4-triazine,
5-(4-dimethylaminophenyl)-6-(4-fluorophenyl)-3-methoxy-1,2,4-triazine,
5-(4-chlorophenyl)-6-(4-fluorophenyl)-3-methyl-1,2,4-triazine,
6-(4-chlorophenyl)-3-neopentyloxy-5-(4-propylphenyl)-1,2,4-triazine,
3-(2,3-dimethylpentylthio)-5-(4-ethylphenyl)-6-(4-isopropoxyphenyl)-1,2,4-triazine,
3-benzyl-5-(4-methylphenyl)-6-(4-propylphenyl)-1,2,4-triazine,
6-(4-dimethylominophenyl)-5-(4-isopropylphenyl)-3-(p-methylbenzyloxy)-1,2,4-triazine,
3-cyclobutyl-5-(4-ethoxyphenyl)-6-(4-ethylphenyl)-1,2,4-triazine, 3-cyclopropyloxy-6-(4-dipropylaminophenyl)-5-(4-fluorophenyl)-1,2,4-triazine,
5,6-bis(4-fluorophenyl)-3-(3-methylcyclohexylthio)-1,2,4-triazine,
5,6-bis(4-ethylphenyl)-3-[2-(3-methylcyclopentyl)ethyl]-1,2,4-triazine,
3-cyclobutylmethoxy-5-(4-diethylaminophenyl)-6-(4-methylphenyl)-1,2,4-triazine,
3-cyclopropylmethylthio-6-(4-fluorophenyl)-5-(4-propylphenyl)-1,2,4-triazine, and the like,
and the pharmaceutically-acceptable acid addition salts of the basic triazines.

The preferred triazines are those wherein at least one of $R_2$ and $R_3$ in the above-defined formula is fluoro or methyl. More preferably, $R_2$ and $R_3$ will be the same, and most preferably are fluoro or methyl. With respect to the substituent in the 3-position, the preferred groups are $C_1$–$C_8$ alkyl (R is —$(X)_nR_1$, n is 0, and $R_1$ is $C_1$–$C_8$ alkyl), $C_1$–$C_8$ alkoxy (R is —$(X)_nR_1$, n is 1, X is O, and $R_1$ is $C_1$–$C_8$ alkyl), and $C_1$–$C_8$ alkylthio (R is —$(X)_nR_1$, n is 1, X is S, and $R_1$ is $C_1$–$C_8$ alkyl). More preferably, the 3-substituent is $C_1$–$C_8$ alkyl or $C_1$–$C_8$ alkoxy. Most preferably, the 3-substituent is $C_1$–$C_3$ alkyl or $C_1$–$C_3$ alkoxy.

Examples of such preferred, more preferred, and most preferred triazines are included in the above list of illustrative triazines.

The compounds of the present invention are prepared by a variety of methods known to those having ordinary skill in the art. Starting materials and intermediates also are prepared by known methods. The preparation of 5,6-diaryl-1,2,4-triazines is described generally by J. G. Erickson in "The 1,2,3- and 1,2,4-Triazines, Tetrazines and Pentazines," The Chemistry of Heterocyclic Compounds, Vol. 10, Interscience Publishers, Inc., New York, N.Y., 1956, Chapter II, pp. 44–84. The 5,6-diaryl-1,2,4-triazines which are unsubstituted in the 3-position can be prepared by the catalytic reduction of the corresponding 3-chlorotriazines.

The specific procedure employed to prepare a given 3-substituted-5,6-diaryl-1,2,4-triazine in part is dependent upon the substituent in the 3-position. For example, 3-alkyl-, 3-aralkyl-, 3-cycloalkyl-, and 3-(cycloalkyl)alkyl-5,6-diaryl-1,2,4-triazines can be prepared directly by the cyclization of acylhydrazones of α-diketones by ammonium acetate in hot acetic acid under controlled conditions; see, e.g., C. M. Atkinson and H. D. Cossey, J. Chem. Soc., 1962, 1805 [Chem. Abstr., 57:4662i (1962)]. Such triazines also can be prepared from 3-chloro-5,6-diaryl-1,2,4-triazines by the procedure of E. C. Taylor and S. F. Martin [J. Amer. Chem. Soc., 94, 2874 (1972)] which involves the nucleophilic displacement of chlorine by a Wittig reagent which may be generated in situ from an alkyl-, aralkyl-, cycloalkyl-, or (cycloalkyl)alkyltriarylphosphonium halide.

3-Chloro-5,6-diaryl-1,2,4-triazines also can be employed to prepare the 3-alkoxy, 3-aralkoxy-, 3-cycloalkoxy-, 3-(cycloalkyl)alkoxy-, 3-alkylthio-, 3-aralkylthio-, 3-cycloalkylthio-, and 3-(cycloalkyl)alkylthio-5,6-diaryl-1,2,4-triazines via the nucleophilic displacement of chlorine by the appropriate alcohol or thiol. The 3-alkylthio-, 3-aralkylthio-, 3-cycloalkylthio-, and 3-(cycloalkyl)alkylthio- compounds can be converted to the 3-alkoxy-, 3-aralkoxy-, 3-cycloalkoxy-, and 3-(cycloalkyl)alkoxy-5,6-diaryl-1,2,4-triazines, again via nucleophilic displacement by the appropriate alcohol. The 3-alkylthio-, 3-aralkylthio-, 3-cycloal-kylthio, and 3-(cycloalkyl)alkylthiotriazines in many cases can be prepared by treating the appropriate 3-mercapto-5,6-diaryl-1,2,4-triazine with the appropriate hydrocarbyl halide in the presence of base, particularly when the hydrocarbyl halide is primary or secondary.

3-Chloro-5,6-diaryl-1,2,4-triazines are readily obtained by treating the appropriate 3-hydroxytriazine with phosphorus oxychloride. 3-Hydroxy- and 3-mercapto-5,6-diaryl-1,2,4-triazines in turn can be prepared by condensing an appropriate benzil with semicarbazide or thiosemicarbazide, respectively.

The required benzils are prepared by the oxidation of the corresponding benzoins with copper sulfate in pyridine; see H. T. Clarke and E. E. Driger, Org. Synthesis, Coll. Vol. I, 87 (1941). The benzoins are prepared by the condensation of aromatic aldehydes with cyanide ion; see W. S. Ide and J. S. Buck, Org. Reactions, 4, 269 (1948).

Another approach to the compounds of the present invention involves the use of benzils having substituents which can be displaced to give the desired $R_2$ or $R_3$ substituent. For example, the halogen on the phenyl ring at the 5-position in 5-(4-halophenyl)-6-aryl-1,2,4-triazines can be displaced with an alcohol or a dialkylamine to give the corresponding 5-(4-alkoxyphenyl)- or 5-(4-dialkylaminophenyl)- compound, respectively.

The use of two different aromatic aldehydes in the benzoin synthesis leads to unsymmetrical benzils. That is, in a benzil of the formula,

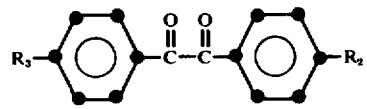

wherein $R_2$ and $R_3$ are as described hereinbefore, $R_2$ and $R_3$ are different. The use of an unsymmetrical benzil may result in the preparation of a mixture of triazine isomers. For example, the condensation of 4-dimethylamino-4'-methoxybenzil with thiosemicarbazide gives a mixture of 5-(4-dimethylaminophenyl)-6-(4-methoxyphenyl)-1,2,4-triazine-3-thiol and 6-(4-dimethylaminophenyl)-5-(4-methoxyphenyl)-1,2,4-triazine-3-thiol.

It will be recognized by those skilled in the art that mixtures of triazine isomers are separable by known methods, such as fractional crystallization and chromatography. The isomer separation may be effected upon intermediate mixtures or delayed until the final product stage.

Certain of the 5,6-diaryl-1,2,4-triazines described herein are sufficiently basic to form acid addition salts, especially when the triazine contains a dialkylamino group on a phenyl ring. "Pharmaceutically-acceptable" acid addition salts are well known to those skilled in the art and are in general are formed by reacting in a mutual solvent a stoichiometric amount of a suitable acid with a basic triazine. Such salts should not be substantially more toxic to warm-blooded animals than the triazines. While the choice of a salt-forming acid is not critical, in some instances a particular acid may result in a salt having special advantages, such as ready solubility, ease of crystallization, and the like. Representative and suitable acids include, among others, the following: hydrochloric, hydrobromic, hydriodic, sulfuric, nitric, phosphoric, methanesulfonic, p-toluenesulfonic, and the like.

A modification of the method of Winder was used to measure the anti-inflammatory activities of the compounds of the present invention; see C. V. Winder et al., *Arch. Int. Pharmacodyn.*, 116, 261 (1958). Albino guinea pigs of either sex, weighing 225–300 grams, were shaved on the back and chemically depilated (Nair Lotion Hair Remover, Carter Products, N.Y., N.Y.) 18–20 hours before exposure to ultraviolet light. The animals, in groups of four and bearing identifying ear tags, were treated by applying to an area of skin of about 12 cm.$^2$ a solution of test compound dissolved in 0.1 cc. of ethanol. The control treatment consisted of administering only the drug vehicle, ethanol, to a group of four animals. Groups of four animals each were given different treatment levels of test compound to obtain dose reponses. Random order and blind administration of the test compounds were employed; drug identification was not made until after all animals were graded. Immediately prior to drug application, the animals were exposed in groups of four to a high-intensity ultraviolet light for a measured period of time (usually 4–7 seconds). The ultraviolet light source, a Hanovia Lamp (Kroymayer-Model 10), was placed in contact with the skin of the animal's back. A gummed notebook paper reinforcement was affixed to the lamp lens to provide an unexposed area of contrast for grading the erythema. Beginning one hour after exposure and thereafter at half-hour intervals for another 1½ hours, the degree of resulting erythema was graded by an arbiturary scoring system based upon the degree of contrast and redness formed. Anti-inflammatory agents delay the development of the erythema and usually have their greatest effect at the initial grading periods. The scores were, therefore, weighted by factors of 4, 3, 2, and 1 at the 1.0, 1.5, 2.0, and 2.5 hour scoring times, respectively. The erythema was graded as follows:

| Score | Erythema Scoring System<br>Appearance of Exposed Area |
|---|---|
| 0 | No redness and no contrast |
| 1 | Slight redness with a faint reinforcement outline |
| 2 | Slight to moderate redness with a distinct outline |
| 3 | Marked redness with a distinct circular outline |

Total scores from each treatment group of four guinea pigs were compared to the control treatment, and the percent inhibition was calculated as follows:

$$100 \times \frac{\text{Control Treatment Score} - \text{Score}}{\text{Control Score}} = \text{Percent Inhibition}$$

A dose-response graph is obtained by plotting dose versus the average percent inhibition of each treatment group of four guinea pigs. The dose ($ED_{50}$) in micrograms per 12 cm.$^2$ (mcg./12 cm.$^2$) which produces a 50% inhibition of the erythemic response for the particular compound tested is obtained by extrapolation. In general, the 5,6-diaryl-1,2,4-triazines of the present invention result in at least about 20 percent inhibition at dose levels below about $10^3$ mcg./12cm.$^2$ For example, 3-methoxy-5,6-bis(4-methylphenyl)-1,2,4-triazine has an $ED_{50}$ of 20.5 mcg./12cm.$^2$, and 5,6-bis(4-fluorophenyl)-3-methylthio-1,2,4-triazine has an $ED_{50}$ of 13 mcg./12cm.$^2$.

The toxicities of representative compounds of the present invention, determined as the dose ($LD_{50}$) in milligrams per kilogram (mg./kg.) of animal body weight which is lethal to 50 percent of mice treated orally, typically are greater than about 1000 mg./kg., and in some cases are greater than about 1500 mg./kg.

In the utilization of the compounds of this invention, one (or more) of the anti-inflammatory triazines is topically administered to a warm-blooded mammal in an amount sufficient to provide at least about 1 mcg./12 cm.$^2$; such administration can be repeated periodically as needed. Because of the relatively low order of toxicity of such triazines, the maximum level of application is limited only by the esthetics of the mode of administration. As a practical matter, however, such triazines normally need not be administered at a level much above about $10^3$ mcg./12 cm.$^2$, although levels of about $10^5$ mcg./12 cm.$^2$ or higher can be employed, if desired.

The topical administration of the anti-inflammatory compounds can be made according to any of the well known prior art procedures. Thus, such administration can utilize aerosols, creams, emulsions, lotions, ointments, solutions, and the like. In each case, the compounds to be employed are utilized in combination with one or more adjuvants suited to the particular mode of application. For example, ointments and solutions for topical administration can be formulated with any of a number of pharmaceutically-acceptable carriers, including ethanol, animal and vegetable oils, mixtures of waxes, solid and liquid hydrocarbons, glycols, and the like. Thus, a typical ointment composition comprises the following ingredients per gram of ointment:

|  | mg. |
|---|---|
| Triazine | 0.1 – 100 |
| Polyethylene glycol 300 (N.F.) | 450 – 700 |
| Polyethylene glycol 4000 (U.S.P.) | 300 – 450 |

The concentration of the anti-inflammatory triazine in the final topical preparation is not critical. In general, such concentration can range from about 0.001 percent to about 50 percent (w/w or w/v), or higher.

The following examples further illustrate the preparations of the compounds of the present invention.

EXAMPLE 1

Preparation of 5,6-Bis(4-fluorophenyl)-3-methylthio-1,2,4-triazine (A) 5,6-Bis(4-fluorophenyl)-3-mercapto-1,2,4-triazine.

A solution of 80 g. of 4,4'-difluorobenzil in 400 ml. of ethanol was heated to reflux. Water then was added to the point of incipient turbidity, followed by the addition of 80 g. of thiosemicarbazide and 96 g. of sodium acetate. The reaction mixture was heated at reflux for one hour. Water again was added to the reaction mixture to the point of incipient turbidity. Sodium hydroxide, 80 g., then was added gradually to the reaction mixture, which then was heated at reflux for 1 hour. The reaction mixture was poured into a 3-fold volume of ice water and aqueous hydrochloric acid was added until the mixture was strongly acidic. The solid which precipitated was isolated by filtration and recrystallized from acetic acid to give 57.5 g. of 5,6-bis(4-fluorophenyl)-3-mercapto-1,2,4-triazine, m.p. about 180°–182° C.

Analysis: $C_{15}H_9F_2N_3S$.
Calc: C, 59.79; H, 3.01; N, 13.95;
Found: C, 59.96; H, 3.12; N, 14.05.

(B) 5,6-Bis(4-fluorophenyl)-3-methylthio-1,2,4-triazine.

To a solution of 26.5 g. of 5,6-bis(4-fluorophenyl)-3-mercapto-1,2,4-triazine and 4 g. of sodium hydroxide in 300 ml. of ethanol was added 24.2 g. of methyl iodide. The mixture was agitated at ambient temperature. The precipitate which formed was isolated by filtration and recrystallized from ethanol, giving 14 g. of 5,6-bis(4-fluorophenyl)-3-methylthio-1,2,4-triazine, m.p. about 134°–136° C.

Analysis: $C_{16}H_{11}F_2N_3S$;
Calc: C, 60.94; H, 3.52; F, 12.05; N, 13.33;
Found: C, 60.72; H, 3.48; F, 11.92; N, 13.04.

EXAMPLE 2

Preparation of 5-(4-Dimethylaminophenyl)-6-(4-fluorophenyl)-3-methylthio-1,2,4-triazine (A) 5-(4-Dimethylaminophenyl)-6-(4-fluorophenyl)-3-Mercapto-1,2,4-triazine.

To a solution of 8.1 g. of 4-dimethylamino-4'-fluorobenzil in 65 ml. of acetic acid was added 3.3 g. of thiosemicarbazide. The reaction mixture then was heated at reflux for three hours. The solid which precipitated was isolated by filtration, washed successively with ethanol and water, and dried, giving 4.3 g. of 5-(4-dimethylaminophenyl)-6-(4-fluorophenyl)-3-mercapto-1,2,4-triazine, m.p. about 262°–264° C.

Analysis: $C_{17}H_{15}FN_4S$;
Calc: C, 62.57; H, 4.63; F, 5.82; N, 17.17;
Found: C, 62.83; H, 4.73; F, 5.70; N, 17.29.

(B) 5-(4-Dimethylaminophenyl)-6-(4-fluorophenyl)-3-methylthio-1,2,4-triazine.

To a solution of 0.48 g. of sodium hydroxide in 100 ml. of ethanol was added 4 g. of 5-(4-dimethylaminophenyl)-6-(4-fluorophenyl)-3-mercapto-1,2,4-triazine. To the resulting solution was added, with agitation, 2.1 g. of methyl iodide. The precipitate which formed was isolated by filtration and recrystallized from ethanol to give 2.9 g. of 5-(4-dimethylaminophenyl)-6-(4-fluorophenyl)-3-methylthio-1,2,4-triazine, m.p. about 144°–146° C.

Analysis: $C_{18}H_{17}FN_4S$;
Calc: C, 63.51; H, 5.03; N, 16.46; S, 9.42;
Found: C, 63.22; H, 5.30; N, 16.24; S, 9.23.

EXAMPLE 3

Preparation of 5,6-Bis(4-methylphenyl)-3-methylthio-1,2,4-triazine (A) 3-Mercapto-5,6-bis(4-methylphenyl)-1,2,4-triazine.

To a solution of 85 g. of 4,4'-dimethylbenzil in 360 ml. of acetic acid heated to about 80°–100° C. was added 35.5 g. of thiosemicarbazide, portionwise, over a 10-minute period. The reaction mixture was heated at reflux for 2 hours. The reaction mixture was cooled and diluted with 500 ml. of water. The solid which precipitated was isolated by filtration, washed with water, and recrystallized from ethanol to give 22 g. of 3-mercapto-5,6-bis(4-methylphenyl)-1,2,4-triazine, m.p. about 220°–223° C.

Analysis: $C_{17}H_{15}N_3S$;
Calc: C, 69.60; H, 5.15; N, 14.32;
Found: C, 69.32; H, 5.36; N, 14.60.

(B) 5,6-Bis(4-methylphenyl)-3-methylthio-1,2,4-triazine.

To a solution of 24 g. sodium hydroxide in about one liter of ethanol was added 146.5 g. of 3-mercapto-5,6-bis(4-methylphenyl)-1,2,4-triazine. To the resulting solution was added 88.2 g. of methyl iodide. The reaction mixture was agitated overnight at ambient temperature. The solid which precipitated was isolated by filtration and washed with ethanol; the solid was recrystallized from ethanol to give 101.1 g. of 5,6-bis(4-methylphenyl)-3-methylthio-1,2,4-triazine, m.p. about 170°–172° C.

Analysis: $C_{18}H_{17}N_3S$;
Calc: C, 70.33; H, 5.57; N, 13.67;
Found: C, 70.25; H, 5.78; N, 13.72.

EXAMPLE 4

Preparation of 3-Methoxy-5,6-bis(4-methylphenyl)-1,2,4-triazine

A solution of sodium methoxide in methanol was prepared by reacting 5 g. of sodium with 350 ml. of methanol. To such solution was added 61.4 g. of 5,6-bis(4-methylphenyl)-3-methylthio-1,2,4-triazine. The reaction mixture was heated at reflux for 6 hours, then was allowed to stir overnight at ambient temperature. The reaction mixture was concentrated under reduced pressure and the residue was diluted with water. The insoluble solid was isolated by filtration and recrystallized from ethanol to give 3-methoxy-5,6-bis(4-methylphenyl)-1,2,4-triazine, m.p. about 125°–128° C.

Analysis: $C_{18}H_{17}N_3O$;
Calc: C, 74.20; H, 5.88; N, 14.42
Found: C, 74.11; H, 5.83; N, 14.17.

What is claimed is:

1. The compound of the formula,

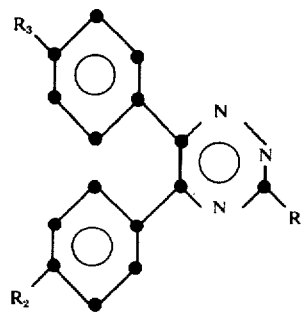

wherein R is hydrogen or $-(X)_nR_1$, in which X is either O or S, $n$ is an integer which is either 0 or 1, and $R_1$ is $C_1$–$C_8$ alkyl, $C_7$–$C_8$ aralkyl, $C_3$–$C_8$ cycloalkyl, or $C_4$–$C_8$ (cycloalkyl)alkyl; and $R_2$ and $R_3$ independently are halo, $C_1$–$C_3$ alkyl, $C_1$–$C_3$ alkoxy, or di($C_1$–$C_3$ alkyl)amino, with the proviso that at least one of $R_2$ and $R_3$ is halo or $C_1$–$C_3$ alkyl; and the pharmaceutically-acceptable acid addition salts of basic members thereof.

2. The compound of claim 1, wherein $R_2$ and $R_3$ are the same and are fluoro or methyl.

3. The compound of claim 1, wherein R is $-(X)_nR_1$, in which $R_1$ is $C_1$–$C_8$ alkyl.

4. The compound of claim 3, wherein $n$ is 0.

5. The compound of claim 3, wherein X is O and $n$ is 1.

6. The compound of claim 3, wherein x is S and $n$ is 1.

7. The compound of claim 3, wherein $R_1$ is $C_1$–$C_3$ alkyl.

8. The compound of claim 7, which compound is 5,6-bis(4-fluorophenyl)-3-methyl-1,2,4-triazine.

9. The compound of claim 7, which compound is 3-methyl-5,6-bis(4-methylphenyl)-1,2,4-triazine.

10. The compound of claim 7, which compound is 5,6-bis(4-fluorphenyl)-3-methoxy-1,2,4-triazine.

11. The compound of claim 7, which compound is 3-methoxy-5,6-bis(4-methylphenyl)-1,2,4-triazine.

12. The compound of claim 7, which compound is 5,6-bis(4-fluorophenyl)-3-methylthio-1,2,4-triazine.

13. The compound of claim 7, which compound is 5,6-bis(4-methylphenyl)-3-methylthio-1,2,4-triazine.

* * * * *